United States Patent [19]
Grey et al.

[11] Patent Number: 5,401,857
[45] Date of Patent: Mar. 28, 1995

[54] PROCESS FOR MAKING γ-BUTYROLACTONES

[75] Inventors: Roger A. Grey, West Chester; Diandre Armstead, Philadelphia, both of Pa.

[73] Assignee: Arco Chemical Technology, L.P., Greenville, Del.

[21] Appl. No.: 203,163

[22] Filed: Feb. 28, 1994

[51] Int. Cl.⁶ .......................... C07D 307/28
[52] U.S. Cl. .................................... 549/295
[58] Field of Search ........................... 549/295

[56] References Cited

U.S. PATENT DOCUMENTS

| | | | |
|---|---|---|---|
| 3,061,614 | 10/1962 | Sweeney et al. | 260/343.6 |
| 3,952,020 | 4/1976 | Stapp | 260/343.6 |
| 4,301,090 | 11/1981 | Pesa et al. | 260/465.4 |
| 4,331,612 | 5/1982 | Pesa et al. | 260/465.4 |
| 4,451,407 | 5/1984 | Pesa et al. | 260/465.4 |
| 4,634,780 | 1/1987 | Alper et al. | 549/273 |

OTHER PUBLICATIONS

Chemistry Letters (1983) 1465–1466.
Alper et al., J. Org. Chem 56 (1991) 5357–5360.
Falbe Ang. Chem. Int. Ed. Eng. 5 (1966) 435–532.

*Primary Examiner*—C. Warren Ivy
*Assistant Examiner*—A. A. Owens
*Attorney, Agent, or Firm*—Jonathan L. Schuchardt

[57] ABSTRACT

A cyclocarbonylation process for making γ-butyrolactones under mild temperature and pressure conditions is disclosed. In the process, an allylic alcohol reacts with carbon monoxide in the presence of a rhodium carbonyl catalyst and an amount of a pyridine promoter effective to enhance the selectivity of the process for making the γ-butyrolactone product. The process provides a way of making γ-butyrolactone from allyl alcohol as the only C4 product.

20 Claims, No Drawings

PROCESS FOR MAKING γ-BUTYROLACTONES

FIELD OF THE INVENTION

The invention relates to a process for making γ-butyrolactones. In particular, the invention is a process for making γ-butyrolactones by reacting allylic alcohols with carbon monoxide in the presence of a rhodium carbonyl catalyst and a pyridine promoter.

BACKGROUND OF THE INVENTION

γ-Butyrolactones are well known solvents and chemical intermediates for complex molecules such as natural products and pharmaceuticals. γ-Butyrolactone, the simplest of these compounds, is a widely used organic solvent, and is produced commercially by several methods. Some γ-butyrolactone is obtained as a by-product in a commercial process for making 1,4-butanediol from allyl alcohol. A potentially attractive route to γ-butyrolactone converts allyl alcohol directly to γ-butyrolactone in a cyclocarbonylation reaction:

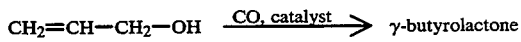

Cyclocarbonylation of allyl alcohol to γ-butyrolactone is known. Matsuda et al. (*Bull. Chem. Soc. Jpn.* 11 (1968) 1876) reported a cobalt carbonyl-catalyzed cyclocarbonylation of allyl alcohol to γ-butyrolactone. The reaction was performed in a $CO/H_2$ atmosphere at high pressure (about 130 atmospheres). High selectivity to γ-butyrolactone resulted when a nitrile solvent and a pyridine promoter were used. Rhodium carbonyl catalysts were not investigated.

Kaneda et al. (*Chem. Lett.* (1983) 1465) reacted allyl alcohol with CO under water-gas shift conditions in the presence of a rhodium carbonyl catalyst and a pyridine promoter, and obtained γ-butyrolactone in 68% yield. The process also gave a 21% yield of another C4 product, 1,4-butanediol. Results from a nonaqueous process were not reported.

Sweeney et al. (U.S. Pat. No. 3,061,614) teach a process for making γ-butyrolactone by carbonylating allyl alcohol in the presence of a cobalt carbonyl catalyst. Water or a $C_1$–$C_4$ alcohol is included in the process as a hydrogen donor, and high pressures (>130 atmospheres) are used. Rhodium catalysts and pyridine promoters are not taught.

Alper et al. (U.S. Pat. No. 4,364,780) teach a process for producing lactones from unsaturated alcohols by cyclocarbonylation in the presence of a protic acid and a bimetallic transition metal catalyst. Pyridine promoters and cyclocarbonylation under neutral conditions are not taught.

An improved process for making γ-butyrolactones from allylic alcohols is needed. A preferred process could be performed at relatively low gas pressures under neutral, non-aqueous conditions. A preferred process would give γ-butyrolactone from allyl alcohol as the only C4 product.

SUMMARY OF THE INVENTION

The invention is a cyclocarbonylation process for making γ-butyrolactones. The process comprises reacting an allylic alcohol with carbon monoxide under nonaqueous conditions in the presence of a rhodium carbonyl catalyst and a pyridine promoter to produce a γ-butyrolactone. We surprisingly found that a pyridine promoter significantly enhances the selectivity of the cyclocarbonylation process toward γ-butyrolactone production when a rhodium carbonyl compound is used as the catalyst. When allyl alcohol is used, γ-butyrolactone is the only C4 product.

We also surprisingly found that the process of the invention can be performed under nonaqueous conditions and at relatively low gas pressures. Although previous work in the ad suggests that water-gas shift conditions are needed for the rhodium-catalyzed cyclocarbonylation process, our results indicate that γ-butyrolactones can be made from allylic alcohols using a rhodium carbonyl catalyst and pyridine promoter under nonaqueous conditions. Also, while pressures in excess of 130 atmospheres have been generally used in this type of process, the present invention can be performed at much lower pressures (e.g., 3–20 atmospheres).

DETAILED DESCRIPTION OF THE INVENTION

In the process of the invention, an allylic alcohol reacts with carbon monoxide in the presence of a rhodium carbonyl catalyst and a pyridine promoter under nonaqueous conditions to give a γ-butyrolactone.

Allylic alcohols suitable for use in the invention contain at least one allylic alcohol moiety. Preferred allylic alcohols have the structure:

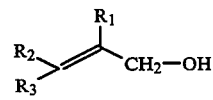

in which each of $R_1$, $R_2$ and $R_3$ separately represents hydrogen or a linear, branched, or cyclic $C_1$–$C_{16}$ alkyl, aryl, or aralkyl group; except that at least one of $R_2$ or $R_3$ is hydrogen. Suitable allylic alcohols include, for example, allyl alcohol, methallyl alcohol, crotyl alcohol, 2-methyl-2-buten-1-ol, 2-phenyl-2-propen-1-ol, 3-phenyl-2-propen-1-ol, 2-octen-1-ol, 2-methyl-2-octen-1-ol, 2-benzyl-2-propen-1-ol, and the like, and mixtures thereof. Allyl alcohol is particularly preferred.

A γ-butyrolactone is produced in the process of the invention. Preferred γ-butyrolactones will have the structure:

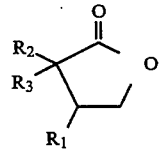

in which $R_1$, $R_2$, and $R_3$ are as described above for the allylic alcohols. Thus, γ-butyrolactones available from the process of the invention include, for example, γ-butyrolactone, α-methyl-γ-butyrolactone, β-methyl-γ-butyrolactone, α-phenyl-γ-butyrolactone, β-dodecyl-γ-butyrolactone, α,β-dimethyl-γ-butyrolactone, β-benzyl-γ-butyrolactone, and the like. Particularly preferred is γ-butyrolactone.

By "rhodium carbonyl catalyst," we mean a rhodium carbonyl compound or a rhodium compound that converts to a rhodium carbonyl compound in the presence of carbon monoxide. Preferred catalysts include rhodium carbonyls; rhodium compounds and rhodium carbonyl compounds that contain complexed ligands such as halides, nitrates, carboxylates, sulfonates, and amines; elemental forms of rhodium; rhodium compounds that contain complexed olefins; and polymer-bound rhodium. Rhodium carbonyl complexes that contain phosphine ligands are generally not preferred; many of these complexes tend to promote hydroformylation of the allylic alcohol while giving little or no cyclocarbonylation product.

Suitable catalysts include, for example, hexarhodium hexadecacarbonyl, tetrarhodium dodecacarbonyl, chlorodicarbonylrhodium (I) dimer, chloronorbonadiene rhodium (I) dimer, chloropentaaminerhodium (III) chloride, dicarbonylacetylacetonato rhodium (I), rhodium (II) acetate dimer, rhodium on alumina, rhodium on carbon, rhodium on silica, bis(1,5-cyclooctadiene)rhodium (I) triflate, chlorobis(ethylene)-rhodium (I) dimer, chloro(1,5-cyclooctadiene)rhodium (I) dimer, rhodium (III) acetylacetonate, rhodium (III) bromide, rhodium (III) chloride, rhodium (III) nitrate, rhodium (II) octanoate dimer, tris(ethylenediamine)rhodium (III) chloride, bis[(pentamethylcyclopentadienyl)dichlororhodium], polyvinylpyridine-bound rhodium, and the like.

The amount of rhodium carbonyl catalyst used depends on many factors, including the allylic alcohol used, the particular catalyst type, the desired reaction rate, and so on. Generally, the rhodium carbonyl catalyst will be used in an amount within the range of about $10^{-6}$ to about $10^{-1}$ moles (as rhodium) per mole of allylic alcohol used. A more preferred range is from about $10^{-5}$ to about $10^{-2}$ moles Rh per mole of allylic alcohol.

A pyridine promoter is used in the process of the invention. The promoter is pyridine or a compound having a pyridine moiety. Suitable pyridine promoters include, but are not limited to, pyridine, (dialkylamino)pyridines, alkylpyridines, arylpyridines, ortho-bipyridines, cyanopyridines, (2-hydroxyethyl)pyridines, phenanthrolines, (pyrrolidino)pyridines, and the like. Specific examples include pyridine, 4-(dimethylamino)pyridine, 3-methylpyridine, 4-ethylpyridine, 4-cyanopyridine, 4-(2-hydroxyethyl)pyridine, 3-phenylpyridine, phenanthroline, 2,2'-bipyridine, and the like. Mixtures of pyridine promoters can be used. Pyridine and (dialkylamino)pyridines are preferred.

The amount of pyridine promoter used is not critical. The required amount of promoter is an amount effective to enhance the selectivity of the process for $\gamma$-butyrolactones compared with the selectivity obtained in the absence of the promoter. Generally, it is preferred to use at least about 0.1 mole of the pyridine promoter per mole of allylic alcohol used. If desired, however, the pyridine promoter can even be used as a solvent (e.g., as much as 100 moles of pyridine promoter per mole of allylic alcohol). A preferred range is from about 0.5 moles to about 2 moles of pyridine promoter per mole of allylic alcohol. Most preferred is the range from about 1 to about 2 moles.

The process of the invention is performed under nonaqueous conditions. Previous rhodium-catalyzed cyclocarbonylation processes for making $\gamma$-butyrolactone used water-gas shift conditions (an equilibrium mixture of water, carbon monoxide, carbon dioxide, and hydrogen). We found that a rhodium-catalyzed, pyridine-promoted cyclocarbonylation process has desirable selectivity under nonaqueous conditions.

An organic solvent is optionally used in the process of the invention. Suitable organic solvents are compounds that do not react with the amine promoter, the allylic alcohol, or the $\gamma$-butyrolactone under the reaction conditions. Suitable solvents include, for example, aliphatic and aromatic hydrocarbons, halogenated hydrocarbons, ethers, ketones, alcohols, nitriles, and the like, and mixtures thereof.

The reaction is performed under an atmosphere of carbon monoxide. If desired, up to about 25 mole percent of hydrogen can be included with the CO, but hydrogen is not necessary. Preferably, the amount of hydrogen present is less than about 5 mole percent. When more than about 25 mole percent of hydrogen is used, the process gives an undesirable amount of hydroformylation products.

Unlike other cyclocarbonylation processes known in the art, the process of the invention can be performed at relatively low gas (CO or CO/H$_2$) pressures. However, any convenient pressure can be used, and the product mixture is generally insensitive to pressure. Although CO or CO/H$_2$ pressures up about 200 atmospheres can be used, it is preferred to maintain the pressure within the range of about 3 to about 20 atmospheres.

The process of the invention can be performed over a broad temperature range. Generally, it is preferred to perform the process at a temperature within the range of about 20° C. to about 150° C. A more preferred range is from about 50° C. to about 100° C. At temperatures greater than about 150° C., competing side reactions become important, while the reaction becomes too slow at temperatures below about 20° C.

The invention provides a way to make $\gamma$-butyrolactones under relatively mild temperature and pressure conditions. In addition, the nonaqueous process of the invention gives good selectivity to $\gamma$-butyrolactones.

The following examples merely illustrate the invention. Those skilled in the art will recognize many variations that are within the spirit of the invention and scope of the claims.

EXAMPLES 1-7

General Procedure for Cyclocarbonylation

A 100-mL Hastelloy C pressure reactor equipped with a glass liner and a mechanical stirrer is charged with allyl alcohol (26 mmol), Rh$_6$(CO)$_{16}$ (0.050 mmol), pyridine promoter (29 mmol, see Table 1 ), and toluene (or 2-ethoxyethanol) (15 g). The reactor is sealed, and the headspace is purged for 15 min. with nitrogen. The reactor is pressurized with carbon monoxide to 300 psi. The reaction mixture is then stirred and heated to 60° C., and is kept at 60° C. for 2-12 h as indicated in Table 1. After cooling the mixture to 23° C., the gases are vented, and the liquid products are analyzed by gas chromatography. Results of the analyses appear in Table 1.

As shown in Table 1, the use of a pyridine promoter (Examples 2-7) enhances the selectivity of the process for $\gamma$-butyrolactone compared with the selectivity obtained in the absence of the promoter (Comparative Example 1). In contrast to the results reported in *Chem. Lett.* (1983) 1465 by Kaneda et al. with water-gas shift conditions, the process of the invention gives no C4 products other than $\gamma$-butyrolactone. In addition, the process of the invention is performed under relatively mild conditions of temperature and pressure.

TABLE 1

Preparation of γ-Butyrolactone from Allyl Alcohol using $Rh_6(CO)_{16}$ and a Pyridine Promoter[1]

| Ex. # | Promoter | Time (h) | % Conv. | Selectivity (%)[2] GBL | PA |
|---|---|---|---|---|---|
| C1* | None | 12 | 20 | 3 | 97 |
| 2 | 4-(dimethylamino)-pyridine | 12 | 32 | 43 | 57 |
| 3 | pyridine | 12 | 78 | 31 | 69 |
| 4 | 4-methylpyridine | 12 | 48 | 32 | 68 |
| 5 | 3,4-dimethylpyridine | 2 | 36 | 28 | 72 |
| 6 | 4-(dimethylamino)-pyridine | 12 | 12 | 32 | 68 |
| 7 | 4-methylpyridine[3] | 2 | 25 | 32 | 68 |

[1]All reactions are performed in toluene at 60° C. except Ex. 6, in which 2-ethoxyethanol is used.
[2]Selectivities measured by gas chromatography; GBL = γ-butyrolactone; PA = propionaldehyde; no C4 products are detected.
[3]Reaction performed with 14% $H_2$ in the CO.
*Comparative example The preceding examples are meant only as illustrations. The following claims define the scope of the invention.

We claim:

1. A cyclocarbonylation process for making a γ-butyrolactone, said process comprising reacting an allylic alcohol with carbon monoxide under nonaqueous conditions in the presence of a rhodium carbonyl catalyst and a pyridine promoter to produce a γ-butyrolactone, wherein the promoter is used in an amount effective to enhance the selectivity of the process for the γ-butyrolactone compared with the selectivity obtained in the absence of the promoter.

2. The process of claim 1 wherein the allylic alcohol has the structure:

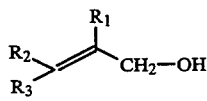

in which each of $R_1$, $R_2$ and $R_3$ separately represents hydrogen or a linear, branched, or cyclic $C_1$-$C_6$ alkyl, aryl, or aralkyl group; except that at least one of $R_2$ or $R_3$ is hydrogen.

3. The process of claim 1 wherein the allylic alcohol is allyl alcohol.

4. The process of claim 1 wherein the rhodium carbonyl catalyst is selected from the group consisting of rhodium carbonyls; rhodium compounds and rhodium carbonyl compounds that contain halides, nitrates, carboxylates, sulfonates, and amines; elemental forms of rhodium; rhodium compounds that contain complexed olefins; and polymer-bound rhodium.

5. The process of claim 1 wherein the rhodium carbonyl catalyst is $Rh_6(CO)_{16}$.

6. The process of claim 1 wherein the amount of rhodium carbonyl catalyst used is within the range of about $10^{-6}$ to about $10^{-1}$ moles of Rh per mole of allylic alcohol.

7. The process of claim 1 wherein the pyridine promoter is selected from the group consisting of pyridine, (dialkylamino)pyridines, alkylpyridines, arylpyridines, ortho-bipyridines, cyanopyridines, (2-hydroxyethyl)-pyridines, phenanthrolines, and (pyrrolidino)pyridines.

8. The process of claim 1 wherein the pyridine promoter is used in an amount within the range of about 0.5 moles to about 2 moles of pyridine promoter per mole of allylic alcohol.

9. The process of claim 1 performed at a CO or $CO/H_2$ pressure within the range of about 3 atmospheres to about 20 atmospheres.

10. A cyclocarbonylation process for making γ-butyrolactone, said process comprising reacting allyl alcohol with carbon monoxide under nonaqueous conditions in the presence of a rhodium carbonyl catalyst and a pyridine promoter to produce γ-butyrolactone, wherein the promoter is used in an amount effective to enhance the selectivity of the process for γ-butyrolactone compared with the selectivity obtained in the absence of the promoter.

11. The process of claim 10 wherein the rhodium carbonyl catalyst is selected from the group consisting of rhodium carbonyls; rhodium compounds and rhodium carbonyl compounds that contain halides, nitrates, carboxylates, sulfonates, and amines; elemental forms of rhodium; rhodium compounds that contain complexed olefins; and polymer-bound rhodium.

12. The process of claim 10 wherein the rhodium carbonyl catalyst is $Rh_6(CO)_{16}$.

13. The process of claim 10 wherein the amount of rhodium carbonyl catalyst used is within the range of about $10^{-6}$ to about $10^{-1}$ moles of Rh per mole of allylic alcohol.

14. The process of claim 10 wherein the pyridine promoter is selected from the group consisting of pyridine, (dialkylamino)pyridines, alkylpyridines, arylpyridines, ortho-bipyridines, cyanopyridines, (2-hydroxyethyl)pyridines, phenanthrolines, and (pyrrolidino)pyridines.

15. The process of claim 10 wherein the pyridine promoter is used in an amount within the range of about 0.5 moles to about 2 moles of pyridine promoter per mole of allylic alcohol.

16. The process of claim 10 performed at a CO or $CO/H_2$ pressure within the range of about 3 atmospheres to about 20 atmospheres.

17. A cyclocarbonylation process for making γ-butyrolactone, said process comprising reacting allyl alcohol with carbon monoxide under nonaqueous conditions at a pressure within the range of about 3 to about 20 atmospheres in the presence of $Rh_6(CO)_{16}$ and a pyridine promoter selected from the group consisting of pyridine and (dialkylamino)pyridines to produce γ-butyrolactone, wherein the promoter is used in an amount effective to enhance the selectivity of the process for γ-butyrolactone compared with the selectivity obtained in the absence of the promoter.

18. The process of claim 17 wherein the $Rh_6(CO)_{16}$ catalyst is used in an amount within the range of about $10^{-5}$ to about $10^{-2}$ moles of Rh per mole of allyl alcohol.

19. The process of claim 17 wherein the pyridine promoter is used in an amount within the range of about 0.5 moles to about 2 moles of pyridine promoter per mole of allyl alcohol.

20. The process of claim 17 wherein the pyridine promoter is 4-(dimethylamino)pyridine.

* * * * *